United States Patent [19]

Oshiro

[11] 4,432,349

[45] Feb. 21, 1984

[54] ARTICULATED TUBE STRUCTURE FOR USE IN AN ENDOSCOPE

[75] Inventor: Susumu Oshiro, Iwatsuki, Japan

[73] Assignee: Fuji Photo Optical Co., Ltd., Omiya, Japan

[21] Appl. No.: 308,602

[22] Filed: Oct. 5, 1981

Related U.S. Application Data

[63] Continuation of Ser. No. 136,727, Apr. 2, 1980, abandoned.

[30] Foreign Application Priority Data

Apr. 3, 1979 [JP] Japan ............................. 54-43183

[51] Int. Cl.³ .......................... A61B 1/00; F16L 11/00
[52] U.S. Cl. ....................................... 128/4; 138/120
[58] Field of Search .................. 128/4, 9, 82; 138/120, 138/155

[56] References Cited

U.S. PATENT DOCUMENTS

| | | | |
|---|---|---|---|
| 3,060,972 | 10/1962 | Sheldon | 128/4 X |
| 3,162,214 | 12/1964 | Bazine, Jr. | 128/42 |
| 3,266,059 | 8/1966 | Stelle | 138/120 X |
| 3,557,780 | 1/1971 | Sato | 128/4 |
| 3,583,393 | 6/1971 | Takahashi | 128/4 |
| 3,799,151 | 3/1974 | Fukaumi | 128/4 X |
| 3,948,251 | 4/1976 | Hosono | 128/4 |

FOREIGN PATENT DOCUMENTS 50-11334  7/1975  Japan .

Primary Examiner—Stephen C. Pellegrino

[57] ABSTRACT

An articulated tube structure for use in an endoscope or the like consists of a number of elementary tubes connected in end-to-end relationship. Between the adjacent elementary tubes are provided springs to urge the articulated tube to bend in one direction. The endoscope is provided with a manipulating box to bend the articulated tube in a desired direction. The articulated tube is spring urged in one direction and is manipulated to bend as desired by operation of pull wires extending through the articulated tube and fixed at their end to the head of the endoscope. The springs may be composed of a series of coil springs provided around one pull wire between adjacent elementary tubes. The spring constant of the coil springs may be increased from the manipulating box to the head so as to bend the articulated tube to more extent in the portion closer to the head than the portion remote from the head.

2 Claims, 2 Drawing Figures

ARTICULATED TUBE STRUCTURE FOR USE IN AN ENDOSCOPE

This is a continuation of application Ser. No. 136,727 filed Apr. 2, 1980 now abandoned.

BACKGROUND OF THE INVENTION

1. Field of the Invention

This invention relates to an articulated tube for use in an endoscope or the like, and more particularly to an articulated tube structure arranged between the head and the flexible tube of an endoscope or the like for permitting the head to be tilted by selective manipulation of pull wires extending through the articulated tube structure and the flexible tube.

2. Description of the Prior Art

The endoscope or the like used for inspection or diagnosis of human body cavities like stomach, intestines and so forth has a long flexible tube to be inserted into the human body or the like. The flexible tube has a head at its end via an articulated tube structure. The articulated tube is bendable to direct the head in a desired direction by manipulation of pull wires extending through the articulated tube and the flexible tube.

In the endoscope, the flexible tube should be long enough to insert the head into deep portions of the body to enhance the performance of the endoscope. Therefore, the endoscope has these days a very long flexible tube. As the length of the flexible tube increases, the friction between the pull wires and the flexible tube increases and the manipulation of the pull wires becomes difficult. Particularly, as the length of the flexible tube increases, the number of bent portions of the flexible tube increases and the friction further increases. As the friction increases, the angle at which the articulated tube is bendable is reduced. With the small angle at which the articulated tube is bendable, it is difficult for the endoscope to be inserted in a complicated cavity. Further, it becomes difficult to inspect deep portions in the cavities. In addition, since an endoscope which cannot be bent at a large angle causes great pain to the human body, it becomes difficult to conduct observation, inspection, diagnosis or medical treatment for a long period of time.

SUMMARY OF THE INVENTION

In view of the above mentioned defects in the prior art endoscopes, the primary object of the present invention is to provide an articulated tube for use in an endoscope or the like which can be bent at a great angle even when the flexible tube connected therewith is long.

Another object of the present invention is to provide an articulated tube for an endoscope or the like which can be bent at a large angle with a small force and simple manipulation.

DESCRIPTION OF THE PREFERRED EMBODIMENTS

Figure 1:
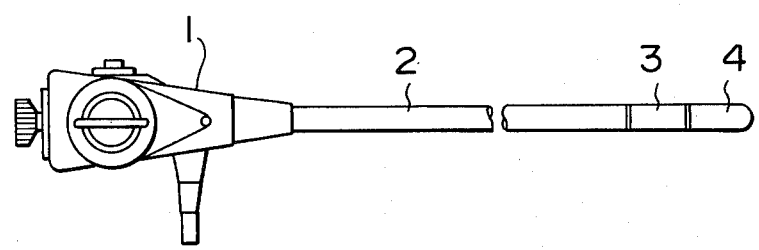
FIG. 1 is a partially cut-away front view of an endoscope in which the articulated tube of this invention may be used.

FIG. 1 shows an endoscope which has an articulated tube 3 between the head 4 and the flexible tube 2 that is connected with a manipulating box 1. The articulated tube 3 is bendable in a desired direction by manipulation of pull wires extending through the flexible tube 2 and the articulated tube 3. The articulated tube 3 is usually bendable in four directions at angular spacings of 90°.

Figure 2:
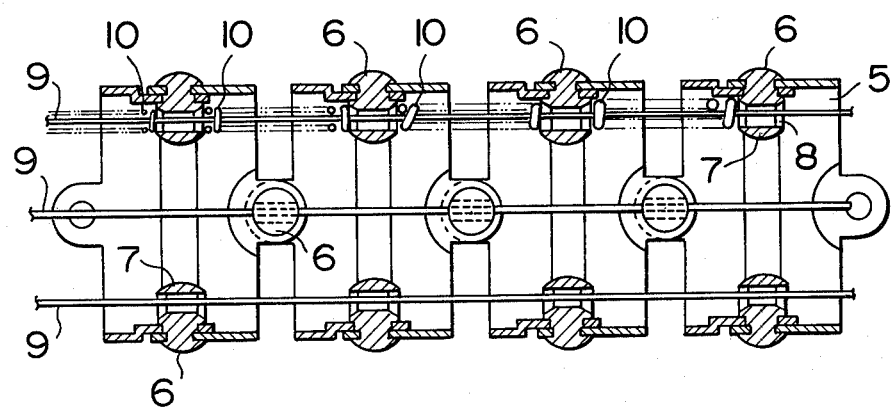
FIG. 2 is a fragmentary longitudinal sectional view of an articulated tube in accordance with an embodiment of this invention.

The articulated tube 3 comprises a series of short elementary tubes 5 as shown in FIG. 2. The series of short elementary tubes 5 are interconnected in end-to-end relationship by means of connecting pins 6 which are provided alternatively at the top and bottom and right and left between the elementary tubes 5. In other words, one elementary tube 5 is connected with the next elementary tube 5 by means of connecting pins 6 provided at the top and bottom of the tubes therebetween. The next elementary tube 5 connected to the first elementary tube 5 is connected in turn with a further next elementary tube 5 by means of connecting pins 6 provided at the right and left sides of the tubes therebetween. The connecting pins 6 are provided with a through hole 8 for passing a pull wire 9 therethrough. Thus, four pull wires 9 are engaged with the connecting pins 6. The top end of the pull wire 9 is fixed to a portion of the head 4 to lift the head in a desired direction by manipulating the pull wires 9. Said through hole 8 is provided in an inwardly projecting extension 7 of the connecting pin 6.

At least one pull wire 9 is provided therearound with coil springs 10 which are compressed between the inwardly projecting extensions 7 of the adjacent connecting pins 6 located at the same position. In other words, between the inwardly projecting extension 7 of a pin 6 at the top between the first and second elementary tubes 5 and the inwardly projecting extension 7 of a pin at the top between the third and fourth elementary tubes 5 is provided a compressed coil spring 10 to urge the second and third elementary tubes 5 in the opposite separating directions. Hence, by the coil springs 10 provided around one pull wire 9, the articulated tube structure is urged to be bent in one direction.

Further, the spring constant of the coil springs 10 is changed or increased from the manipulating box side to the head side so that the coil spring 10 located closer to the head 4 has a larger spring constant, and accordingly, the articulated tube structure is bent to a greater degree at the portion closer to the head 4. Further, when the articulated tube structure is manipulated to be in one direction by releasing the pull wire 9 and allowing the coil springs 10 to bend the articulated tube structure by the spring force thereof, the articulated tube structure starts to bend from the portion closer to the head 4.

Accordingly, the articulated tube structure as mentioned above can be bent at a great angle at the portion close to the head 4 without using a large force. Further, by simply letting the coil springs 10 work on the elementary tubes 5 the articulated tube structure can be bent at a desired angle without using a large force. Therefore, it is possible to direct the head 4 of the endoscope in the desired direction even in a narrow and complicated body cavity.

It should be noted that the coil springs 10 may not be provided throughout the length of the pull wire 9, but may be provided only over a part of the articulated tube structure, close to the head 4 for instance. The spring constant of the coil springs may not be changed continuously but may be changed stepwisely at proper steps. Further, the coil springs 10 may not necessarily be of compression type but may be of expansion type. Furthermore, it should be noted that the coil springs 10 may have the same spring constant but have different degrees of compression or expansion. Further, the coil springs 10 may be provided on a plurality of pull wires 9 to make it possible to bent the articulated tube structure in more than one direction by the spring force. It will be also noted that the oppositely located pull wires 9 could be provided with different types of coil springs, i.e. compression springs on one side and expansion springs on the other, so that the articulated tube structure may be bent to a great extent by the spring force. Further, it will also be noted that the coil springs 10 may be replaced with other types of spring means, like an elastic tube or pad.

I claim:

1. An articulated tube structure for use in an endoscope connected between a head for inspection and a flexible tube which is connected with a manipulating box, said articulated tube structure comprising a number of elementary tubes connected in end-to-end relationship to form an articulated tube, connecting means for connecting the elementary tubes in such a manner that the articulated tube composed thereof is bendable, spring means for urging the articulated tube to bend in one direction, and manipulating means including pull wires extending through the elementary tubes along several sides of the articulated tube for bending the articulated tube in one direction by pulling one of the pull wires on one side of the tube and in another direction by pulling another pull wire on another side thereof, for allowing the articulated tube to bend by the force of said spring means, said spring means comprising a number of coil springs each inserted between adjacent elementary tubes, one coil spring being close to the head and another close to the manipulating box, the spring constant of the coil spring close to the head being larger than that of the coil spring close to the manipulating box.

2. An articulated tube structure for use in an endoscope or the like comprising a number of elementary tubes connected in end-to-end relationship to form an articulated tube, connecting means for connecting the elementary tubes in such a manner that the articulated tube composed thereof is bendable, spring means connected between adjacent elementary tubes on one side of the articulated tube for urging the articulated tube to bend in one direction, and manipulating means including pull wires extending through the elementary tubes along several sides of the articulated tube for bending the articulated tube in one direction by pulling one of the pull wires on one side of the tube and in another direction by pulling another pull wire on another side thereof, for allowing the articulated tube to bend by the force of said spring means, said connecting means comprising connecting pins provided between adjacent elementary tubes for pivotally connecting the same, each connecting pin having an inwardly extending portion provided with a through hole through which one of said pull wires passes, said spring means comprising a series of coil springs respectively provided between adjacent elementary tubes around one of said pull wires.

* * * * *